US006946149B2

(12) United States Patent  (10) Patent No.: US 6,946,149 B2
Cleveland  (45) Date of Patent: Sep. 20, 2005

(54) SALT SOLUTION FOR COLON CLEANSING

(75) Inventor: Mark vB. Cleveland, Duxbury, MA (US)

(73) Assignee: Braintree Laboratories, Inc., Braintree, MA (US)

( * ) Notice: Subject to any disclaimer, the term of this patent is extended or adjusted under 35 U.S.C. 154(b) by 311 days.

(21) Appl. No.: 10/135,857

(22) Filed: Apr. 30, 2002

(65) Prior Publication Data

US 2003/0202957 A1 Oct. 30, 2003

(51) Int. Cl.[7] ...................... A61K 33/04; A61K 31/045; A61K 31/075; A61K 33/00
(52) U.S. Cl. ...................... 424/709; 424/713; 514/723; 514/738; 514/892
(58) Field of Search ................................ 424/709, 713; 514/723, 738, 892

(56) References Cited

U.S. PATENT DOCUMENTS

| | | | | |
|---|---|---|---|---|
| 4,975,286 A | * | 12/1990 | Hechter ....................... | 424/682 |
| 5,077,048 A | * | 12/1991 | Kimura et al. ............... | 424/422 |
| 5,124,144 A | * | 6/1992 | Giorgetti et al. .......... | 424/78.01 |
| 5,197,950 A | | 3/1993 | Clayton ....................... | 604/28 |
| 5,616,346 A | | 4/1997 | Aronchick | |
| 5,710,183 A | | 1/1998 | Halow ........................ | 514/892 |
| 5,997,906 A | | 12/1999 | Wood et al. | |
| 6,162,464 A | | 12/2000 | Jacob et al. | |
| 6,235,745 B1 | * | 5/2001 | Megens ....................... | 514/272 |

OTHER PUBLICATIONS

STN/CAS online, file TOXCENTER, Acc. No. 2002:312828 (Antioquia Med. (1972) 22 (9–10), pp. 699–704), Abstract.*
See STN/CAS online, file CAPLUS, Acc. No. 1980:99549 (Majallah—Daneshgah–e Tehran, Daneshkade–e Darusazi (1976), (Feb.), pp. 28–41), Abstract.*
Martindale (28th Ed. 1982), pp. 626–629,632,643.*
Drug Facts and Comparisons (1994), pp. 1710–1713.*
Adams, et al., "Bisacodyl Reduces the Volume of Polyethylene Glycol Solution Required for Bowel Preparation", Colorectal Unit, St. George Hospital, Sydney, Australia, Dis Colon Rectum, pp. 229–235 (1994).
Bokemeyer, "Koloskopievorbereitung in der ambulanten Gastroenterologis", Verdauungskrankheiten, pp. 17–24 (2000).
Brady, et al., "Effect of Bisacodyl on Gut Lavage Cleansing For Colonoscopy", Annals of Clinical Research, vol. 19, pp. 34–38 (1987).
Clarkston, et al., "The Use of GoLYTELY and Dulcolax in Combination in Outpatient Colonoscopy", J. Clin Gastroenternol, vol. 17(2), pp. 146–148 (1993).
Grundel, et al., "Improvements in Mechanical Bowel Preparation for Elective Colorectal Surgery", Dis Colon Rectum, vol. 40(11), pp. 1348–1352 (1997).

Lind, et al., "Peroral emptying of the colon. A Randomized comparison of 4 and 1.5 liter regimens", Tidssky Nor Laegenforen, vol. 110(11), pp. 1357–1358, (1990).
Sharma, et al., "Prospective, randomized, controlled comparison of the use of polyethylene glycol electrolyte lavage solution in four–liter versus two–liter volumes and pretreatment with either magnesium citrate or bisacodyl for colonoscopy preparation", Gastrointestinal Endoscopy, vol. 47(2), pp. 167–171 (1998).
Villien, et al., "Golytely Preparation for Colonoscopy: 1.5 Liters is Enough for Outpatients", Endoscopy, vol. 22, pp. 168–170 (1990).
"Safety of Sodium Phosphates Oral Solution" Sep. 17, 2001, Food and Drug Administration Science Background, U.S. Food & Drug Administration, Center for Drug Evaluation and Research.
InKine Pharmaceutical Company, Inc. package insert 2000, Visicol Tablets.
Chan, A., et al., Use of Oral Sodium Phosphate Colonic Lavage Solution by Canadian Colonscopists: Pitfalls and Complications, Canadian Journal of Gastroenterology, May/Jun. 1997, 334–338, vol. 11, No. 4, Queen's University, Kingston, Ontario, Canada.
Ahmed, M., et al., Oral Sodium Phosphate Catharsis and Acute Renal Failure, American Journal of Gastroenterology, Jun. 1996, 1261–1262, vol. 91, No. 6, Catholic Medical Center of Brooklyn Queens, Inc., Jamaica, New York, USA.
Dipalma, Ja., et al., Biochemical Effects of Oral Sodium Phosphate, Digestive Diseases and Sciences, Apr. 1996, 749–753, vol. 41, No. 4, Picnum Publishing Corporation, Mobile, Alabama, USA.
Kolts, Byron E., M.D., F.A.C.P., et al., A Comparison of the Effectiveness and Patient Tolerance of Oral Sodium Phosphate, Castor Oil, and Standard Electrolyte Lavage for Colonoscopy or Sigmoidoscopy Preparation, American Journal of Gastroenterology, Aug. 1993, 1218–1223, vol. 88, No. 8, University of Florida Health Science Center, Jacksonville, Florida, USA.

(Continued)

Primary Examiner—S. Mark Clardy
Assistant Examiner—Frank I. Choi
(74) Attorney, Agent, or Firm—Wilmer Cutler Pickering Hale and Dorr LLP

(57) ABSTRACT

The field of colonic diagnostic and surgical procedures is hampered by the lack of optimal means available to cleanse the colon. A compromise between convenient, distasteful, solid or low volume, hyperosmotic solutions which cause considerable fluid and electrolyte imbalances in patients and large volume, difficult to consume, iso-osmotic solutions has had to be made heretofore. This invention describes a low volume, hyper-osmotic solution consisting of sulfate salts with and with out polyethylene glycol. Unlike prior art, this composition is useful for the cleansing of the bowel and, in lower volumes, as a laxative, without producing clinically significant changes in bodily function.

23 Claims, No Drawings

OTHER PUBLICATIONS

Vanner, SJ., et al., A Randomized Prospective Trial Comparing Oral Sodium Phophate with Standard Polyethylene glycol–based lavage solution (Golytely) in the Preparation of Patients for Colonoscopy, American Journal of Gastroenterology, Apr. 1990, 422–427, vol. 85, No. 4, Queen's University, Kingston, Ontario, Canada.

Davis, Gr., et al., Development of a Lavage Solution Associated with Minimal Water and Electrolyte Absorption or Secretion, Gastroenterology, May 1980, 991–995, vol. 78, Baylor University Medical Center, Dallas, Texas, USA.

* cited by examiner

SALT SOLUTION FOR COLON CLEANSING

BACKGROUND OF THE INVENTION

1. Field of the Invention

I have found a new improved concentrated colonic purgative formulation made by combining inorganic salts and polyethylene glycol (PEG) in a small volume of water. This formulation is effective to produce colonic purging to prepare the colon for surgical or diagnostic procedures and surprisingly does not cause clinically significant changes in electrolyte balance.

2. Background Information

In sigmoidoscopy, colonoscopy, radiographic examination, preparation for patients undergoing bowel surgery, and other medical or diagnostic procedures on the colon, it is important that the colon be thoroughly purged and cleaned. In particular, it is essential that as much fecal matter as possible be removed from the colon to permit adequate visualization of the intestinal mucosa. This is important prior to, for example, diagnositc procedures such as flexible sigmoidoscopy or colonoscopy, diagnostic examinations widely performed to screen patients for diseases of the colon. In addition, it is important that the intestines be cleansed thoroughly in order to obtain satisfactory radiographs of the colon. The same condition also applies when the colon is preoperatively prepared for surgery, where removal of fecal waste materials is critically important for patient safety.

Large volume orally administered compositions have been developed for use as gastrointestinal washes for diagnostic purposes or for use as cathartic laxatives. Such orally administered preparations are usually formulated as dilute or isotonic solutions of electrolytes such as sodium sulfate, sodium bicarbonate, sodium chloride and potassium chloride. These orally administered compositions are useful in the rapid cleansing of the colon for diagnostic purposes. These formulations may include other agents such as polyethylene glycol. These formulations have generally been administered in a quantity of about four liters as isotonic solutions. One example composition is GoLYTELY® formulated according to the following: polyethylene glycol 59 g, sodium sulfate 5.68 g, sodium bicarbonate 1.69 g, sodium chloride 1.46 g, potassium chloride 0.745 g and water to make up one liter (Davis et al. Gastroenterology 1980;78:991–995).

Commercially available products embodying these formulations sometimes utilize polyethylene glycol, a non-absorbable osmotic agent, with an isotonic mixture of electrolytes for replenishment, so that patients do not become dehydrated or experience clinically significant electrolyte shifts. Because the solutions are isotonic, patients are required to ingest a significant amount of volume of these solutions, up to one eight ounce glass every ten minutes for a total of one gallon of fluid, to achieve effective purging Sodium sulfate and phosphate salts have been used as laxatives when diluted in a small volume (~300 mL) concentrated solution and taken in tablespoon sized (15 ml) daily doses. An example of this use is Glauber's Salt's (containing sodium sulfate). However, because of their small volumes, when used in this fashion they do not sufficiently clean the colon for diagnostic or surgical procedures. Also these small volume preparations do not contain polyethylene glycol. Sodium sulfate combined with polyethylene glycol and various other salts, administered in large volumes (1 gallon) over a short period of time is an effective gastrointestinal lavage, which cleanses the colon prior to colonoscopy or surgical procedures as described above.

The large volume required for effective use of this type of formulation for lavage is frequently associated with distention, nausea, vomiting and significant patient discomfort. Thus, while these formulations are generally effective, they are not well tolerated.

Another drawback of these prior art preparations is their unpleasant, bitter, saline taste. This can promote nausea and vomiting in sensitive patients—thereby preventing ingestion. It is difficult to overcome this unpleasant taste, even the most common natural sweeteners such as glucose, fructose, saccharose, and sorbitol could change the osmolarity of these orally administered solutions resulting in potentially dangerous electrolyte imbalances.

In an attempt to avoid the problems associated with the high volume types of preparations, other investigators have utilized ingestible preparations which consist of aqueous solutions of concentrated phosphate salts. The aqueous phosphate salt concentrate produces a tremendous osmotic effect on the intra-luminal contents of the bowel and therefore, evacuation of the bowel occurs with a large influx of water and electrolytes into the colon from the body. These phosphate salt preparations have been developed for the purpose of decreasing the volume required in colonic purgations. One such preparation basically is comprised of 480 grams per liter monobasic sodium phosphate and 180 grams per liter dibasic sodium phosphate in stabilized buffered aqueous solution and is sold under the brand name Fleets Phospho-Soda.™. Patients are typically required to take two (2) three ounce doses of this preparation, separated by a three to 12 hour interval for a total of six ounces (180 ml), which is a significant reduction compared to the large 1 gallon volumes required by the high volume preparations. Additionally, non-aqueous tablet or capsule formulations of sodium phosphates and sulfates have been used (U.S. Pat. Nos. 5,997,906, 6,162,464, and 5,616,346).

These small volume sulfate/phosphate solutions and non-aqueous formulations have been shown to cause massive electrolyte and fluid shifts that are clinically significant to the patient (US Food and Drug Administration, Center for Drug Evaluation and Research, Sep. 17, 2001; 2002 Physician's Desk Reference, prescribing information for Fleet's Phospho Soda and InKine Pharmaceutical's Visicol®). The terms "clinically significant" as used herein are meant to convey alterations in blood chemistry that are outside the normal upper or lower limits of their normal range or other untoward effects. These solutions are hyperosmotic; that is the electrolyte concentration of the solution is much higher than the electrolyte concentration in the human body. Available products, as Fleet's Phospho-Soda, and the solid dosage form such as Visicol tablets (sodium phosphate salts) are examples of small volume electrolyte preparations. All of these products have been seen to cause clinically significant electrolyte disturbances and fluid shifts, and disturbances in cardiac and renal function when administered to patients (US Food and Drug Administration, Center for Drug Evaluation and Research, Sep. 17, 2001).

To overcome the risks and electrolyte disturbances that occur with the small volume laxative preparations, large volume "lavage" solutions were developed to be isotonic. Preparing a patient for a surgical or diagnostic procedure on the colon with such an isotonic lavage would result in only minimal fluid and electrolyte shifts in the patient.

GoLytely®, NuLytely®, and CoLyte® are examples of such large volume ravages. Because these lavages are isotonic, the patient experiences minimal, non-clinically significant fluid and electrolyte shifts, if any, upon their administration.

From the foregoing, it can be seen that the two approaches to colonic lavage have significant drawbacks that have not been resolved by prior attempts. The isotonic solutions, while not causing clinically significant fluid or electrolyte shifts, are, of necessity, of large volume, and difficult for patient ingestion. The hypertonic solutions or concentrated non-aqueous formulations are sometimes inadequate to prepare the colon and more importantly, can cause clinically significant electrolyte and fluid shifts, which have been known to cause deaths. Thus, it is desirable to have a small volume orally administered colonic purgative formulation which may be easily and conveniently administered and which avoids the clinically significant problems and objectionable tastes of known formulations. It can also be seen that it is desirable to have such a purgative formulation which may be administered without the large volumes necessary in conventional formulations and which avoids other potentially irritant chemicals or chemicals which could effect osmolality. In the nearly 20 years since the advent of large volume colonic lavage solutions, there has not been success in discovering an effective small volume gastrointestinal cleansing preparation that minimized fluid or electrolyte shifts. Concentrating the large volume lavages into smaller volumes does not achieve the same effectiveness, and is not as safe. This is because the components are not soluble in the small volumes necessary and because the concentrations are such that dangerous electrolyte shifts could occur. One purpose of the present research was to develop a safe, effective, and well tolerated small volume solution made up of a high concentration of poorly absorbable salts that induce a colon cleansing catharsis after oral ingestion without clinically significant alternation of sodium, chloride, bicarbonate, potassium, calcium, and phosphate level and balance or other untoward effects on the recipient.

SUMMARY OF THE INVENTION

I now disclose easily and conveniently administered dosage formulations of effective colonic purgatives.

The disclosed colonic purgative formulations provide safe and effective purgative activity at lower dosages of salt than prior art sodium phosphate tablets, solutions of phosphates and sulfates, or combinations thereof. In addition, a lower volume of fluid is ingested and there are no clinically significant changes in body electrolyte chemistry.

This colonic purgative can be administered with a minimum amount of patient discomfort and is better tolerated than prior art purgatives.

The colonic purgative may include an effective amount of one or more sulfate salts, $Na_2SO_4$, $MgSO_4$, and $K_2SO_4$ have been used. Polyethylene glycol may also be advantageously added to the colonic purgative composition.

DETAILED DESCRIPTION OF AN ILLUSTRATIVE EMBODIMENT

There are two currently used methods used for colonic lavage. These are: (1) gastrointestinal lavage with 4 liters of a balanced solution that causes negligible net water or electrolyte absorption or secretion or (2) oral ingestion of small volumes of concentrated (hypertonic) sulfate or sodium phosphate solutions, e.g. Fleet Phospho-Soda, or the non-aqueous tablet formulations of phosphates or salts, all of which cause clinically significant effects on bodily chemistry.

Clinical trials have shown use of the 4 liter balanced solution to be safe and efficacious. However, compliance is poor because of the large volume of solution that must be rapidly ingested. Additionally, these large volume solutions are not well tolerated by patients.

Use of the hypertonic sodium phosphate solutions is also efficacious in cleansing the colon. However, use of hypertonic sodium phosphate has been shown to cause upset in electrolyte balance including: hyperphosphatemia, hypocalcemia, positive sodium balance, and negative potassium balance. For example, in one published study the average serum phosphate concentration rose from 2.8 to 6.5 mg/dL (Kolts et al., Am. J. Gastroenterology, 88:1218–1223, 1993), and in another some patients developed serum phosphate concentrations as high as 11.6 mg/dL (Vanner et al., Am. J. Gastroenterology 85:422–427, 1990). The normal range for serum phosphate is generally considered to be 2.6 to 4.5 mg/dL. Also, serum potassium fell to as low as 2.9 mEq/L, while the normal range is 3.4 to 5.4. In a third published study, the Ca×P product rose from 35 to as high as 104, while the normal range is generally 22–47 (DiPalma et al., Digestive Diseases and Sciences, 41:749–753, 1996).

Hypertonic phosphate gastrointestinal cleansing solutions have also been associated with hypokalemia and hypocalcemia in some patients, resulting in serious injury and even death (Ahmed et al. Am. J. Gastro. 1998;91:1261–1262).

While Fleet Phospho-Soda preparation, and other hypertonic phosphate colonic lavages are generally considered safe for most healthy adults, they pose significant risks for adverse reactions in patients with renal, cardiac or hepatic diseases, and elderly patients in whom excess sodium absorption might be dangerous. Because of these risks of severe adverse reactions, renal and cardiac function should be evaluated and serum phosphate and serum calcium should be carefully monitored in all patients using hypertonic phosphate gastric lavage composition (Fleet and Visicol labeling). This monitoring is inconvenient, adds to expense and is infrequently performed resulting in dangerous incidents (Chan et al. Can. J. Gastro 1997; 11:334–338).

I have found a safe and effective small volume colonic purgative formulation that avoids the problems of the prior art, using poorly absorbable sulfate salts with a small quantity of polyethylene glycol. In performing this research, my objective was to find a well tolerated orally administered colonic purgative that was as effective as the well known hypertonic phosphate ravages, that avoided the risks of upset of electrolyte balance in patients.

I have found that hypertonic solutions of non-phosphate salts are effective in producing colonic purgation. Addition of an osmotic laxative agent such as polyethylene glycol improves the results in improved purgation and reduces the amounts of salts required. Because it is administered in small volumes, these formulations are better tolerated than formulations now used. These formulations are as effective as colonic purgatives now used, with a lower risk of adverse reactions.

Mixtures of sulfate salts that omit phosphates (which are avidly absorbed) can be effective to produce colonic purgation. In particular, formulations comprising effective amounts of one or more of the following sulfate salts $Na_2SO_4$, $MgSO_4$, and $K_2SO_4$ are effective. Dosage amounts of $Na_2SO_4$ from about 0.01 g to about 40.0 g can be effective to produce purgation. Doses of from about 0.1 g to about 20.0 g may be advantageously used. Dosages of 1.0 to 10.0 g may be preferred. Dosage amounts of $MgSO_4$ from about 0.01 g to about 40.0 g can be effective to produce purgation.

Doses of from about 0.1 g to about 20.0 g may be advantageously used. Dosages of 1.0 to 10.0 g may be preferred. Dosage amounts of $K_2SO_4$ from about 0.01 g to about 20.0 g can be effective to produce purgation. Doses of from about 0.1 g to about 10.0 g may be advantageously used. Dosages of about 0.5 to about 5.0 g may be preferred. The formulation is advantageously a mixture of the foregoing salts.

Addition of an osmotic laxative agent, such as polyethylene glycol (PEG) improves the effectiveness of the above salt mixtures. Doses of PEG from about 1.0 to about 100 g are effective to produce Taxation. Doses from about 10.0 g to about 50 g of PEG have been shown to be effective. A dose of about 34 g of PEG has been used.

For ease of administration, the above mixture of salts can be dissolved in a convenient volume of water. A volume of less than one liter of water is well tolerated by most patients. The mixture can be dissolved in any volume of water, and volumes of between 100 and 500 ml are often convenient. Any volume may be administered. Optimally, the effective dose may be divided and administered, to the patient in two, or more administrations over an appropriate time period. Generally, 2 doses administered of equal portions of the effective dose, separated by 6 to 24 hours produce satisfactory purgation

EXAMPLES

Subjects were otherwise healthy adults between the ages of 18 and 55. There were no preferences or exclusions based on gender or ethnic background.

Dietary Preparation and Ingestion of Salt Solution

Each experiment began at midnight on the first day of a two day study period, and was completed at noon on the next day. The subjects did not consume any food or beverages after midnight on day 1. From 6 a.m. until 6 p.m. on day 1 the subjects consumed a clear liquid diet. Clear liquids included strained fruit juices without pulp (apple, white grape, lemonade), water, clear broth or bouillon, coffee or tea (without milk or non-dairy creamer), carbonated and non-carbonated soft drinks, Kool-Aid® (or other fruit flavored drinks), Jell-O® gelatin (without added fruits or toppings), and ice PopSicles® fruit bars. Solid foods, milk, and milk products are not allowed. The subjects kept a record of exactly what they consumed on day 1, and they were asked to consume the same liquids at the same time if and when they did subsequent studies with a different solution.

Subjects reported to the laboratory at 6 p.m. on day 1. At 7 p.m. they ingested the first dose of concentrated salt solution, either Fleet Phospho-Soda or the experimental solution, followed by 8 ounces of water. Eight ounces of water was also ingested at 8, 9, and 10 p.m.

At 5 a.m. on day 2, a second dose of the concentrated salt solution was ingested, followed by 8 ounces of water.

Formulation of Concentrated Salt Solutions:

Fleet Phospho-Soda (C. S. Fleet Co., Inc., Lynchburg, Va. 24506), 90 mL, was added to 240 mL of water, for a volume of 330 mL. One half of this diluted solution was ingested by the subjects on two occasions, at 7 p.m. on day 1 and again at 5 a.m. on day 2. Based on the manufacturer label, the 330 mL of ingested Phospho-Soda solution contained $NaH_2PO_4.H_2O$ (43.2 g) and $Na_2HPO_{40}.7H_2O$ (16.2 g).

The ingested experimental solutions were also 330 mL in volume, and their composition is shown in the tables below. All salts were obtained from Mallinckrodt (Paris, Ky. 40361) and Polyethylene glycol (PEG) was obtained from J. T. Baker (Phillipsburg, N.J. 08865). One half of each experimental solution was ingested by the subjects on two occasions, at 7 p.m. on day 1 and at 5 a.m. on day 2.

TABLE 1

The dosage of ingested salts (mmoles) were as follows:

| | Experimental Solutions | | | | | |
|---|---|---|---|---|---|---|
| | Fleet | A | B | C | D | E |
| $NaH_2PO_4.H_2O$ | 313 | 0 | 0 | 157 | 0 | 0 |
| $Na_2HPO_4.7H_2O$ | 60 | 0 | 0 | 30 | 0 | 0 |
| $Na_2SO_4$ | 0 | 100 | 125 | 142.5 | 142.5 | 142.5 |
| $MgSO_4$ | 0 | 100 | 125 | 0 | 142.5 | 142.5 |
| $K_2SO_4$ | 0 | 0 | 12.5 | 23.75 | 23.75 | 20 |
| KCl | 0 | 5 | 0 | 0 | 0 | |
| $KHCO_3$ | 0 | 5 | 0 | 0 | 0 | |

TABLE 2

The concentration of the salts expressed in millequivalents was:

| | Experimental Solutions | | | | | |
|---|---|---|---|---|---|---|
| | Fleet | A | B | C | D | E |
| Na | 433 | 200 | 250 | 502 | 285 | 285 |
| K | 0 | 10 | 25 | 48 | 48 | 40 |
| Mg | 0 | 200 | 250 | 0 | 285 | 285 |
| $SO_4$ | 0 | 400 | 525 | 333 | 618 | 610 |
| $PO_4$ | 11.6 | 0 | 0 | 5.8 | 0 | 0 |
| Cl | 0 | 5 | 0 | 0 | 0 | 0 |
| $HCO_3$ | 0 | 5 | 0 | 0 | 0 | 0 |

Solution E also contained 34 g of Polyethylene glycol (PEG).

Observations and Measurements:

Body weight was measured at 6:45 p.m. on day 1, and at noon on day 2. Blood pressure (lying and after standing for 30 seconds) was measured every two hours, starting at 6:45 p.m. on day 1 and finishing at 11:45 a.m. on day 2. Blood was drawn at 6:45 p.m. on day 1 and at 6 a.m., 8 a.m., 10 a.m. and 12 noon on day 2. Blood was analyzed for calcium, sulfate, magnesium, phosphate, sodium, chloride, potassium, bicarbonate, osmolality, albumin, total protein, BUN, creatinine, and hematocrit.

Each stool was quantitatively collected in separate containers and its weight and consistency were measured. The degree to which the stool contained fecal material was graded, using a scale from 0–5 (0 would be similar to urine, 5 would be a large amount of solid fecal material). Stools collected from 7 p.m. (day 1) until 5 a.m. (day 2) were pooled: this pool represents the effects of the first dose of salts. Stools collected from 5 a.m. until 12 noon were pooled; this pool represents the effect of the second dose of salts. The electrolyte composition of the two pooled specimens was measured (osmolality, Na, K, Cl, $HCO_3$, $PO_4$, $S_4$, Ca and Mg).

Urine was quantitatively collected from 6 a.m. until 6 p.m. on day 1 (prior to ingestion of salts), from 7 p.m. on day 1 until 5 a.m. on day 2, and from 5 a.m. on day 2 until 12 noon on day 2. Urine was analyzed for sulfate, phosphate, calcium, magnesium and monovalent electrolytes.

Results

Study results are shown in tables 3 and 4.

TABLE 3

Fecal And Urine Analysis

| | Intake | FECAL Output | Change | URINE Output (mL) |
|---|---|---|---|---|
| Volume (mL) | | | | |
| Phospho-Soda Experimental Solution | 1530 | 2403 | −873 | 902 |
| A | 1530 | 1510 | 20 | 832 |
| B | 1530 | 2209 | −679 | 789 |
| C | 1530 | 1868 | −338 | 779 |
| D | 1530 | 2202 | −672 | 639 |
| E | 1530 | 2729 | −1199 | 780 |
| Sodium (mEq) | | | | |
| Phospho-Soda Experimental Solution | 437 | 397 | 40 | −80 |
| A | 200 | 198 | 2 | 89 |
| B | 200 | 302 | −102 | 109 |
| C | 502 | 360 | 142 | 169 |
| D | 285 | 331 | −46 | 132 |
| E | 285 | 369 | −84 | 95 |
| Potassium (mEq) | | | | |
| Phospho-Soda Experimental Solution | 0 | 54 | −54 | 29 |
| A | 10 | 30 | −20 | 19 |
| B | 20 | 41 | −21 | 21 |
| C | 48 | 34 | 14 | 44 |
| D | 48 | 44 | 4 | 28 |
| E | 40 | 42 | −2 | 24 |
| Chloride (mEq)) | | | | |
| Phospho-Soda Experimental Solution | 0 | 41 | −41 | 42 |
| A | 5 | 36 | −31 | 53 |
| B | 0 | 71 | −71 | 82 |
| C | 0 | 21 | −21 | 81 |
| D | 0 | 71 | −71 | 86 |
| E | 0 | 81 | −81 | 62 |
| Bicarbonate (mEq) | | | | |
| Phospho-Soda Experimental Solution | 0 | 19 | −19 | |
| A | 5 | 38 | −33 | 0 |
| B | 0 | 61 | −61 | 0 |
| C | 0 | 16 | −16 | 0 |
| D | 0 | 89 | −89 | 0 |
| E | 0 | 72 | −72 | 0.9 |
| Phosphorous (g) | | | | |
| Phospho-Soda Experimental Solution | 10.6 | 6.5 | 4.1 | 1.7 |
| A | 0 | 0.1 | −0.1 | 0.3 |
| B | 0 | 0.2 | −0.2 | 0.2 |
| C | 5.8 | 2.3 | 3.5 | 0.3 |
| D | 0 | ND | 0 | 0.4 |
| E | 0 | 0.13 | −0.1 | 0.3 |
| Calcium (mEq) | | | | |
| Phospho-Soda Experimental Solution | 0 | 5 | −5 | 1.7 |
| A | 0 | 9 | −9 | 7 |
| B | 0 | 11 | −11 | 5 |
| C | 0 | 3 | −3 | 3 |
| D | 0 | 8 | −8 | 8 |
| E | 0 | 17 | −17 | 6 |
| Magnesium (mEq) | | | | |
| Phospho-Soda Experimental Solution | 0 | 9 | −9 | 1.8 |
| A | 200 | 156 | 44 | 6 |
| B | 200 | 193 | 7 | 5 |
| C | 0 | 3 | −3 | 2 |
| D | 285 | 187 | 98 | 7 |
| E | 285 | 239 | 46 | 7 |
| Sulfate (mEq) | | | | |
| Phospho-Soda Experimental Solution | 0 | 12 | −12 | 11 |
| A | 400 | 285 | 115 | 65 |
| B | 420 | 370 | 50 | 55 |
| C | 333 | 210 | 123 | 74 |
| D | 618 | 433 | 185 | 63 |
| E | 610 | 478 | 132 | 58 |
| PEG (g) | | | | |
| Phospho-Soda Experimental Solution | 0 | 0 | 0 | 0 |
| A | 0 | 0 | | |
| B | 0 | 0 | | 0 |
| C | 0 | 0 | | 0 |
| D | 0 | 0 | | 0 |
| E | 34 | 29.1 | | 4.9 |

TABLE 4

Serum Electrolyte and Mineral Data

| | 645 PM | 600 AM | 800 AM | 10 AM | 1200 PM |
|---|---|---|---|---|---|
| Sodium (mEq/L) | | | | | |
| Phospho-Soda Experimental Solution | 138 | 141 | 142 | 143 | 143 |
| A | 138 | 139 | 140 | ND | ND |
| B | 140 | 142 | 141 | 142 | 142 |
| C | 141 | 142 | 144 | 144 | 144 |
| D | 136 | 139 | 138 | 138 | 138 |
| E | 140 | 141 | 142 | 141 | 142 |
| Potassium (mEq/L) | | | | | |
| Phospho-Soda Experimental Solution | 4.9 | 3.7 | 3.9 | 4.0 | 3.9 |
| A | 5.4 | 4.0 | 4.2 | ND | ND |
| B | 5.7 | 4.4 | 4.7 | 4.9 | 4.4 |
| C | 5.5 | 4.2 | 4.6 | 4.6 | 4.5 |
| D | 7.3 | 4.2 | 4.6 | 4.2 | 4.2 |
| E | 4.6 | 4.0 | 4.3 | 4.4 | 4.3 |
| Chloride (mEq/L)) | | | | | |
| Phospho-Soda Experimental Solution | 103 | 105 | 107 | 107 | 107 |
| A | 107 | 104 | 106 | ND | ND |
| B | 107 | 106 | 108 | 108 | 107 |
| C | 106 | 107 | 109 | 110 | 109 |
| D | 108 | 106 | 107 | 107 | 106 |
| E | 105 | 105 | 107 | 107 | 107 |

TABLE 4-continued

Serum Electrolyte and Mineral Data

| | 645 PM | 600 AM | 800 AM | 10 AM | 1200 PM |
|---|---|---|---|---|---|
| Bicarbonate (mEq/L) | | | | | |
| Phospho-Soda Experimental Solution | 23 | 23 | 21 | 22 | 23 |
| A | 21 | 23 | 23 | ND | ND |
| B | 20 | 21 | 19 | 21 | 20 |
| C | 23 | 22 | 22 | 22 | 23 |
| D | 24 | 23 | 21 | 21 | 21 |
| E | 23 | 24 | 23 | 22 | 23 |
| Sulfate (mEq/L) | | | | | |
| Phospho-Soda Experimental Solution | 1.63 | 1.68 | 1.52 | 1.75 | 1.70 |
| A | 1.16 | 1.79 | 1.84 | ND | ND |
| B | 1.92 | 1.75 | 1.83 | 1.58 | 1.83 |
| C | 1.38 | 1.86 | 1.54 | 1.70 | 1.78 |
| D | 0.88 | 1.30 | 1.62 | 1.46 | 1.30 |
| E | 1.36 | 1.85 | 2.01 | 1.87 | 1.62 |
| Phosphorous (mg/dL) | | | | | |
| Phospho-Soda Experimental Solution | 3.3 | 6.5 | 7.9 | 6.3 | 5.4 |
| A | 2.6 | 3.1 | 2.8 | ND | ND |
| B | 2.8 | 3.1 | 2.8 | 2.8 | 2.9 |
| C | 3.1 | 5.9 | 6.6 | 5.8 | 4.4 |
| D | 3.2 | 2.7 | 2.7 | 2.7 | 2.8 |
| E | 3.3 | 3.3 | 3.3 | 3.2 | 3.2 |
| Calcium (mg/dL) | | | | | |
| Phospho-Soda Experimental Solution | 9.2 | 9.1 | 8.9 | 9.0 | 9.1 |
| A | 9.2 | 9.3 | 9.5 | ND | ND |
| B | 9.4 | 9.6 | 9.4 | 9.5 | 9.5 |
| C | 9.4 | 9.3 | 9.3 | 9.2 | 9.5 |
| D | 8.9 | 9.1 | 8.8 | 9.0 | 8.7 |
| E | 9.3 | 9.5 | 9.7 | 9.6 | 9.6 |
| Ca × P | | | | | |
| Phospho-Soda Experimental Solution | 30.2 | 59.7 | 70.7 | 56.5 | 48.9 |
| A | 23.9 | 28.8 | 26.6 | ND | ND |
| B | 26.3 | 29.8 | 26.3 | 26.6 | 27.6 |
| C | 29.1 | 54.9 | 61.4 | 53.4 | 41.8 |
| D | 28.5 | 24.6 | 23.8 | 24.3 | 24.4 |
| E | 30.9 | 31.5 | 32.2 | 30.4 | 30.3 |
| Magnesium (mg/dL) | | | | | |
| Phospho-Soda Experimental Solution | 2.0 | 2.1 | 2.1 | 2.2 | 2.2 |
| A | 2.3 | 2.6 | 2.6 | ND | ND |
| B | 2.3 | 2.7 | 2.6 | 2.7 | 2.7 |
| C | 2.3 | 2.4 | 2.3 | 2.3 | 2.4 |
| D | 1.8 | 2.0 | 1.9 | 1.9 | 1.9 |
| E | 2.0 | 2.3 | 2.4 | 2.5 | 2.4 |
| Hematocrit | | | | | |
| Phospho-Soda Experimental Solution | 40.0 | 42.3 | 41.8 | 43.8 | 43.1 |
| A | 38.5 | 39.8 | 39.3 | ND | ND |
| B | 37.8 | 41.1 | 39.8 | 39.5 | 39.5 |
| C | 35.3 | 36.8 | 37.0 | 36.7 | 37.2 |
| D | 37.1 | 39.7 | 40.1 | 40.2 | 40.8 |
| E | 38.8 | 40.8 | 41.7 | 42.8 | 42.9 |

As indicated in table 3, stool volume averaged 2403 mL in three subjects who ingested the standard dose of Phospho-Soda. Table 4 shows that this was associated with a clinically significant rise in serum phosphate, a clinically significant fall in serum calcium, a clinically significant rise in serum calcium×phosphate product (Ca×P), and a large net gastro intestinal potassium loss of 54 mEq. Serum potassium also fell, but generally stayed in the normal range. However, all subjects had a net negative balance in potassium. Serum phosphorus increased markedly, well outside of the normal range.

Solution A contained 100 mmoles of $Na_2SO_4$ and 100 mmoles of $MgSO_4$, as well as small amounts of KCl and $KHCO_3$ to replace anticipated K, Cl, and $HCO_3$ losses. After ingestion of solution A, stool output (1500) was short of the Phospho-Soda output benchmark (2403 ml).

For solution B $K_2SO_4$ was substituted for KCl and $KHCO_3$; the $Na_2SO_4$ and $MgSO_4$ contents were each increased to 125 mmoles. Fecal output rose with solution B, to 2209 mL, but as shown in table 4 the potassium losses were unacceptably high.

The effect of adding phosphate salts was investigated in solution C which contained one half of the amount of phosphate in the Fleet Phospho-Soda protocol, and 142.5 mmoles of $Na_2SO_4$. This solution resulted in 1868 mL of fecal output. However, there was substantial net sodium absorption from this solution, and the serum Ca×P product increased dramatically due to absorbed phosphate. We therefore decided that phosphate should be excluded completely from further experimental solutions.

Solution D contained 142.5 mmoles of both $Na_2SO_4$ and $MgSO_4$, and 23.75 mmoles of $K_2SO_4$. This solution resulted in a stool volume of 2202 mL, which was slightly (180 mL) short of benchmark. Electrolyte changes were clinically insignificant with this formulation. A further increase in the ingested amounts of salts would likely be effective but, we were concerned about taste problems.

For solution E, PEG 3350 was added and the $K_2SO_4$ content reduced slightly as compared to solution D. In two subjects, solution E produced an average fecal output that slightly exceeded the Phospho-Soda benchmark, and the taste was acceptable. This solution caused no increase in Ca×P product, and its effect on potassium balance appeared to be close to zero. A small clinically insignificant change, was seen for magnesium, which stayed within the normal range of 1.4 to 3.1 mg/dL. Changes in sodium, chloride, sulfate and bicarbonate balance with this solution were considered to be of no clinical significance.

There are two ways to estimate the degree to which the poorly absorbable solutes were absorbed by the intestine. The first involves subtraction of fecal output from oral intake. This method assumes that anything not excreted in the stool by the end of the experiment was absorbed. Using this method, the absorption of phosphate after ingesting of Fleet Phospho-soda was 4.0 grams, or 38% of the ingested phosphate load.

The absorption of sulfate after ingestion of solution E was 165 mEq, or 27% of the ingested load. However, the serum sulfate concentration remained well below the level at which calcium sulfate precipitates form, therefore calcium levels remained unchanged. The absorption of magnesium after ingestion of solution E was 66 mEq, or 23% of the ingested load. The second method that can be used involves changes in urine output of the solutes. When a phosphate-free solution was ingested (solution E), urine phosphate excretion was 0.4 g, whereas when 10.6 g of phosphate were ingested (Fleet Phospho-Soda), urine phosphate excretion was 2.1 g (=1.7 g); thus, 16% of the ingested phosphate appeared in the collected urine. By a similar calculation, 10% of ingested sulfate and 2% of ingested magnesium appeared in the collected urine. By both methods, the intestinal absorption of the ingested electrolytes occurred in the following order of magnitude: P>SO$_4$>Mg.

The volume of fecal fluid output, the quality of colonic cleansing, side effects, and weight loss were similar with Fleet Phospo-Soda and Solutions D and E. Both solutions were unpleasant to ingest, but neither had a bad aftertaste. The highest observed Ca×P product varied from 62 to 76 with Phospho-Soda which is well in excess of the level at which calcium-phosphate precipitates form. For solution E Ca×P was from 30 to 37. The Phospho-Soda preparation caused a net gastrointestinal loss of 54 mEq of potassium, whereas solutions D and E caused essentially no loss or gain of potassium.

The serum phosphate concentration increased more than 2-fold after ingestion of Phospho-Soda, whereas the serum sulfate concentration rose only slightly after ingestion of solution E. There were no significant changes in serum magnesium concentration.

Solution E contains three sulfate salts (Na$_2$SO$_4$, K$_2$SO$_4$ and MgSO$_4$) as well as polyethylene glycol. Sulfate, magnesium and polyethylene glycol are poorly absorbed, and ingestion of this solution therefore induces osmotic diarrhea. The sodium content of solution E is less than the sodium content of Phospho-Soda, and solution E contains potassium whereas Phospho-Soda does not. Solution E and Fleet Phospho-Soda appear to provide equivalent colonic cleansing. However, in contrast to Phospho-Soda, solution E does not cause serum phosphate concentration to rise and does not cause a net gastrointestinal loss of potassium.

Both solutions were associated with approximately 2.5 kg loss in body weight which can be explained by higher water output (in both stool and in urine) than water intake by mouth. To prevent this weight loss, the subjects would need to ingest an additional 2.5 kg of water, which would increase total water intake to approximately 4 liters. This might be advisable for protection of body fluid volume, but it might make the method of cleansing less attractive and less convenient. There were no changes in the vital signs of our subjects, indicating that the observed body water losses caused by ingestion of the two solutions are well tolerated by normal people.

The Phopho-Soda phosphate solution and solutions D and E produce similar volumes of osmotic diarrhea, and the quality of colon cleansing (as judged by examination of fecal fluid) with the two solutions were similar. Presumably, both solutions will be associated with some residual colonic fluid, which is not a problem during colonoscopy since such fluid is readily aspirated via the suction lumen of the colonoscope. However, for virtual colonscopy it is desirable that the colon be dry, and to this end of Ducolax suppository is often employed shortly before CT scanning is performed.

The foregoing description is illustrative of the preferred embodiments shown. It is not intended to limit the present invention to the specific formulations shown and described, but instead it will be appreciated that adaptations and modifications will become apparent from the present disclosure and are intended to be within the scope of the claims. For example, small amounts of sodium chloride, potassium chloride and or bicarbonate may be added to consider patient needs.

What is claimed is:

1. A composition for inducing purgation of the colon of a patient, the composition comprising a small volume of an aqueous hypertonic solution which comprises an effective amount of one or more salts selected from the group consisting of Na$_2$SO$_4$, MgSO$_4$, and K$_2$SO$_4$, and an effective amount of PEG, wherein the composition does not produce any clinically significant electrolyte shifts and does not include phosphate.

2. A composition according to claim 1, wherein the solution comprises an effective amount of Na$_2$SO$_4$, an effective amount of MgSO$_4$, an effective amount of K$_2$SO$_4$, and an effective amount of PEG.

3. A composition according to claim 2, wherein the solution comprises between about 2 grams and about 40 grams of Na$_2$SO$_4$, between about 2 grams and about 20 grams of MgSO$_4$, between about 1 gram and about 10 grams of K$_2$SO$_4$, and between about 0.1 gram and about 50 grams of PEG.

4. A composition for inducing purgation of the colon of a patient according to claim 1, wherein the solution comprises about 20 grams of Na$_2$SO$_4$, about 20 grams of MgSO$_4$, about 3 grams of K$_2$SO$_4$, and about 34 grams of PEG.

5. A composition for inducing purgation of the colon of a patient according to claim 4, wherein the solution has a volume of less than 500 ml.

6. A composition for inducing purgation of the colon of a patient, comprising a small volume of an aqueous hypertonic solution consisting essentially of an effective amount of one or more salts selected from the group consisting of Na$_2$SO$_4$, MgSO$_4$, and K$_2$SO$_4$, and an effective amount of PEG, wherein the composition does not produce any clinically significant electrolyte shifts and does not include phosphate.

7. A composition for inducing purgation of the colon of a patient according to claim 6, wherein the solution consists essentially of about 20 grams of Na$_2$SO$_4$, about 20 grams of MgSO$_4$, about 3 grams of K$_2$SO$_4$, and about 34 grams of PEG in about 330 ml of water.

8. A composition according to claim 1, wherein the solution is from about 100 ml to about 500 ml in volume.

9. A composition according to claim 1, wherein the solution comprises an effective amount of two or more salts selected from the group consisting of Na$_2$SO$_4$, MgSO$_4$, and K$_2$SO$_4$, and an effective amount of PEG.

10. A method for inducing colonic purgation in a patient, comprising the steps of:
    (a) orally administering an effective amount of the composition of claim 1 to a patient; and
    (b) allowing the administered composition to induce colonic purgation.

11. A method for inducing colonic purgation according to claim 10, wherein the solution consists essentially of about 20 grams of Na$_2$SO$_4$, about 20 grams of MgSO$_4$, about 3 grams of K$_2$SO$_4$, and about 34 grams of PEG in about 330 ml of water.

12. A method for inducing colonic purgation in a patient according to claim 10, wherein the effective amount of the composition is administered in two or more doses within a treatment period.

13. The method of claim 10, wherein about 100 ml to about 500 ml of the solution is administered to the patient.

14. The method of claim 10, wherein the solution comprises an effective amount of two or more salts selected from group the consisting of Na$_2$SO$_4$, MgSO$_4$, and K$_2$SO$_4$, and an effective amount of PEG.

15. A composition for inducing purgation of the colon of a patient, the composition comprising a small volume of an aqueous hypertonic solution comprising an effective amount of Na$_2$SO$_4$, an effective amount of MgSO$_4$, and an effective amount of K$_2$SO$_4$, wherein the composition does not produce any clinically significant electrolyte shifts and does not include phosphate.

16. A composition according to claim 15, wherein the solution comprises between about 2 grams and about 40 grams of $Na_2SO_4$, between about 2 grams and about 20 grams of $MgSO_4$, and between about 1 gram and about 10 grams of $K_2SO_4$.

17. A composition according to claim 15, wherein the solution is from about 100 ml to about 500 ml in volume.

18. A composition for inducing purgation of the colon of a patient comprising a small volume of an aqueous hypertonic solution consisting essentially of an effective amount of $Na_2SO_4$, an effective amount of $MgSO_4$, and an effective amount of $K_2SO_4$, wherein the composition does not produce any clinically significant electrolyte shifts and does not include phosphate.

19. A method for inducing colonic purgation in a patient, comprising the steps of:
(a) orally administering an effective amount of the composition of claim 18 to a patient; and
(b) allowing the administered composition to induce colonic purgation.

20. A method for inducing colonic purgation in a patient, comprising the steps of:
(a) orally administering an effective amount of the composition of claim 15 to a patient; and
(b) allowing the administered composition to induce colonic purgation.

21. The method of claim 20, wherein about 100 ml to about 500 ml of the solution is administered to the patient.

22. A method for inducing colonic purgation according to claim 20, wherein the solution consists essentially of about 20 grams of $Na_2SO_4$, about 20 grams of $MgSO_4$, and about 3 grams of $K_2SO_4$.

23. A method for inducing colonic purgation in a patient according to claim 20, wherein the effective amount of the composition is administered in two or more doses within a treatment period.

* * * * *

UNITED STATES PATENT AND TRADEMARK OFFICE
CERTIFICATE OF CORRECTION

PATENT NO. : 6,946,149 B2 Page 1 of 1
APPLICATION NO. : 10/135857
DATED : September 20, 2005
INVENTOR(S) : Mark vB. Cleveland et al.

It is certified that error appears in the above-identified patent and that said Letters Patent is hereby corrected as shown below:

Title Page, Item (75) Inventors: should read: -- Mark vB. Cleveland, Duxbury, MA (US)
John S. Fordtran, Dallas, TX (US) --

Signed and Sealed this

Ninth Day of February, 2010

David J. Kappos
*Director of the United States Patent and Trademark Office*

(12) EX PARTE REEXAMINATION CERTIFICATE (6907th)
United States Patent
Cleveland

(10) Number: US 6,946,149 C1
(45) Certificate Issued: Jun. 30, 2009

(54) SALT SOLUTION FOR COLON CLEANSING

(75) Inventor: Mark vB. Cleveland, Duxbury, MA (US)

(73) Assignee: Braintree Laboratories, Inc., Braintee, MA (US)

Reexamination Request:
No. 90/010,316, Oct. 15, 2008

Reexamination Certificate for:
Patent No.: 6,946,149
Issued: Sep. 20, 2005
Appl. No.: 10/135,857
Filed: Apr. 30, 2002

(51) Int. Cl.
*A61K 31/765* (2006.01)
*A61K 31/77* (2006.01)
*A61K 31/74* (2006.01)
*A61K 33/06* (2006.01)

(52) U.S. Cl. .................. 424/709; 424/713; 514/723; 514/738; 514/892

(58) Field of Classification Search ............. None
See application file for complete search history.

(56) References Cited

FOREIGN PATENT DOCUMENTS

| EP | 0298655 | 1/1989 |
| EP | 0396165 A1 * | 7/1990 |
| EP | 0900562 A1 * | 10/1999 |
| WO | WO/00/44240 A1 * | 9/2000 |

OTHER PUBLICATIONS

Abstract to JP 01132527A issued to Morishita on May 25, 1989.*

Parfitt, K., Editor, "Martindale, The Complete Drug Reference" 32nd Edition, 2000, pp. 1157–1159, 1161–1162, 1213–1215, and 1597–1598.*

* cited by examiner

*Primary Examiner*—Dwayne C Jones

(57) ABSTRACT

The field of colonic diagnostic and surgical procedures is hampered by the lack of optimal means available to cleanse the colon. A compromise between convenient, distasteful, solid or low volume, hyperosmotic solutions which cause considerable fluid and electrolyte imbalances in patients and large volume, difficult to consume, iso-osmotic solutions has had to be made heretofore. This invention describes a low volume, hyper-osmotic solution consisting of sulfate salts with and with out polyethylene glycol. Unlike prior art, this composition is useful for the cleansing of the bowel and, in lower volumes, as a laxative, without producing clinically significant changes in bodily function.

US 6,946,149 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 6, 8, 9, 13, 14, 17 and 21 are cancelled.

Claims 2–4, 7, 10, 15 and 18 are determined to be patentable as amended.

Claims 5, 11, 12, 16, 19, 20, 22 and 23, dependent on an amended claim, are determined to be patentable.

2. A composition [according to claim 1] *for inducing purgation of the colon of a patient, the composition comprising from about 100 ml to about 500 ml of an aqueous hypertonic solution*, wherein the solution comprises an effective amount of $Na_2SO_4$, an effective amount of $MgSO_4$, an effective amount of $K_2SO_4$, and an effective amount of PEG, *wherein the composition does not produce any clinically significant electrolyte shifts and does not include phosphate*.

3. A composition according to claim [1] *2*, wherein the solution comprises between about 2 grams and about 40 grams of $Na_2SO_4$, between about 2 grams and about 20 grams of $MgSO_4$, between about 1 gram and about 10 grams of $K_2SO_4$, and between about 0.1 gram and about 50 grams of PEG.

4. A composition for inducing purgation of the colon of a patient according to claim [1] *2*, wherein the solution comprises about 20 grams of $Na_2SO_4$, about 20 grams of $MgSO_4$, about 3 grams of $K_2SO_4$, and about 34 grams of PEG.

7. A composition for inducing purgation of the colon of a patient [according to claim 6], *comprising from about 100 ml to about 500 ml of an aqueous hypertonic solution,* [wherein the solution consists] *consisting* essentially of about 20 grams of $Na_2SO_4$, about 20 grams of $MgSO_4$, about 3 grams of $K_2SO_4$, and about 34 grams of PEG [in about 330 ml of water] *wherein the composition does not produce any clinically significant electrolyte shifts and does not include phosphate*.

10. A method for inducing colonic purgation in a patient, comprising the steps of:
 (a) orally administering an effective amount of the composition of claim [1] *2* to a patient; and
 (b) allowing the administered composition to induce colonic purgation.

15. A composition for inducing purgation of the colon of a patient, the composition comprising [a small volume] *from about 100 ml to about 500 ml* of an aqueous hypertonic solution comprising an effective amount of $Na_2SO_4$, an effective amount of $MgSO_4$, and an effective amount of $K_2SO_4$, wherein the composition does not produce any clinically significant electrolyte shifts and does not include phosphate.

18. A composition for inducing purgation of the colon of a patient, comprising [a small volume] *from about 100 ml to about 500 ml* of an aqueous hypertonic solution consisting essentially of an effective amount of $Na_2SO_4$, an effective amount of $MgSO_4$, and an effective amount of $K_2SO_4$, wherein the composition does not produce any clinically significant electrolyte shifts and does not include phosphate.

* * * * *